United States Patent
Muhanna

(10) Patent No.: US 8,920,502 B1
(45) Date of Patent: Dec. 30, 2014

(54) VERTEBRAL BODY REPLACEMENT

(75) Inventor: Nabil L. Muhanna, Gainesville, GA (US)

(73) Assignee: Spinal USA, Inc., Parsippany, NJ (US)

( * ) Notice: Subject to any disclaimer, the term of this patent is extended or adjusted under 35 U.S.C. 154(b) by 833 days.

(21) Appl. No.: 11/937,242

(22) Filed: Nov. 8, 2007

Related U.S. Application Data

(60) Provisional application No. 60/864,857, filed on Nov. 8, 2006.

(51) Int. Cl.
*A61F 2/44* (2006.01)

(52) U.S. Cl.
USPC ....................................................... 623/17.16

(58) Field of Classification Search
USPC ............................................ 623/17.11–17.16
See application file for complete search history.

(56) References Cited

U.S. PATENT DOCUMENTS

| | | | | |
|---|---|---|---|---|
| 4,657,550 | A * | 4/1987 | Daher | 623/17.11 |
| 5,236,460 | A * | 8/1993 | Barber | 623/17.15 |
| 5,290,312 | A * | 3/1994 | Kojimoto et al. | 623/17.15 |
| 5,306,310 | A | 4/1994 | Siebels | |
| 5,702,455 | A * | 12/1997 | Saggar | 623/17.15 |
| 5,980,522 | A * | 11/1999 | Koros et al. | 623/17.11 |
| 6,176,881 | B1 * | 1/2001 | Schar et al. | 623/17.11 |
| 6,352,556 | B1 | 3/2002 | Kretschmer et al. | |
| 6,524,341 | B2 * | 2/2003 | Lang et al. | 623/17.15 |
| 6,758,862 | B2 | 7/2004 | Berry et al. | |
| 6,866,682 | B1 * | 3/2005 | An et al. | 623/17.15 |
| 6,908,485 | B2 | 6/2005 | Crozet et al. | |
| 6,964,686 | B2 * | 11/2005 | Gordon | 623/17.14 |
| 6,991,653 | B2 | 1/2006 | White et al. | |
| 7,309,358 | B2 | 12/2007 | Berry et al. | |
| 7,458,988 | B2 * | 12/2008 | Trieu et al. | 623/17.13 |
| 8,673,011 | B2 * | 3/2014 | Theofilos et al. | 623/17.16 |
| 2001/0056302 | A1 * | 12/2001 | Boyer et al. | 623/17.15 |
| 2002/0128716 | A1 * | 9/2002 | Cohen et al. | 623/17.15 |
| 2003/0074064 | A1 * | 4/2003 | Gerbec et al. | 623/16.11 |
| 2004/0172129 | A1 * | 9/2004 | Schafer et al. | 623/17.11 |
| 2004/0181283 | A1 * | 9/2004 | Boyer et al. | 623/17.11 |
| 2004/0267364 | A1 * | 12/2004 | Carli et al. | 623/17.14 |
| 2005/0096744 | A1 * | 5/2005 | Trieu et al. | 623/17.11 |
| 2005/0113924 | A1 * | 5/2005 | Buttermann | 623/17.13 |
| 2005/0187634 | A1 * | 8/2005 | Berry | 623/17.15 |
| 2005/0216084 | A1 * | 9/2005 | Fleischmann et al. | 623/17.11 |
| 2006/0058877 | A1 * | 3/2006 | Gutlin et al. | 623/17.11 |
| 2006/0058879 | A1 * | 3/2006 | Metz-Stavenhagen | 623/17.15 |
| 2006/0129241 | A1 * | 6/2006 | Boyer et al. | 623/17.15 |
| 2006/0200244 | A1 | 9/2006 | Assaker | |
| 2006/0241762 | A1 * | 10/2006 | Kraus | 623/17.11 |
| 2006/0293755 | A1 | 12/2006 | Lindner et al. | |
| 2007/0129805 | A1 * | 6/2007 | Braddock et al. | 623/17.11 |
| 2007/0129806 | A1 * | 6/2007 | Harms et al. | 623/17.13 |
| 2007/0255410 | A1 * | 11/2007 | Dickson et al. | 623/17.11 |

(Continued)

*Primary Examiner* — Matthew Lawson
(74) *Attorney, Agent, or Firm* — Knobbe, Martens, Olson & Bear, LLP.

(57) ABSTRACT

This invention concerns a vertebral body replacement element to be inserted into an intervertebral space, thus supporting the spinal column of a patient. The vertebral body replacement element has a first member and a hollow second member, with the upper member and lower member engaging in a telescopic manner between the two members when assembled. Spacers may be inserted to adjustably define the length of the installed vertebral body placement element. The present invention further concerns a system and method for expanding and distracting a vertebral body replacement element into and within the spinal column of a patient.

22 Claims, 3 Drawing Sheets

(56) References Cited

U.S. PATENT DOCUMENTS

| | | | |
|---|---|---|---|
| 2007/0270957 A1* | 11/2007 | Heinz | 623/17.11 |
| 2007/0288092 A1* | 12/2007 | Bambakidis | 623/17.11 |
| 2008/0058931 A1* | 3/2008 | White et al. | 623/17.11 |
| 2008/0138083 A1* | 6/2008 | Lee et al. | 398/155 |
| 2009/0005874 A1* | 1/2009 | Fleischmann et al. | 623/17.16 |
| 2009/0048673 A1* | 2/2009 | Le Huec | 623/17.11 |
| 2009/0112320 A1* | 4/2009 | Kraus | 623/17.11 |
| 2009/0112324 A1* | 4/2009 | Refai et al. | 623/17.16 |
| 2009/0112325 A1* | 4/2009 | Refai et al. | 623/17.16 |
| 2009/0138089 A1* | 5/2009 | Doubler et al. | 623/17.16 |

\* cited by examiner

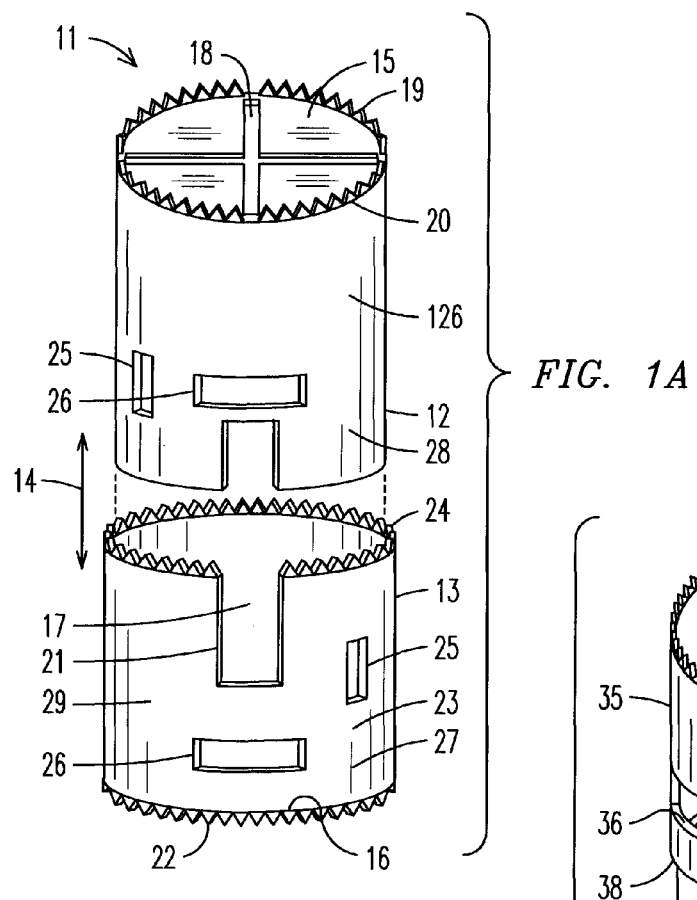
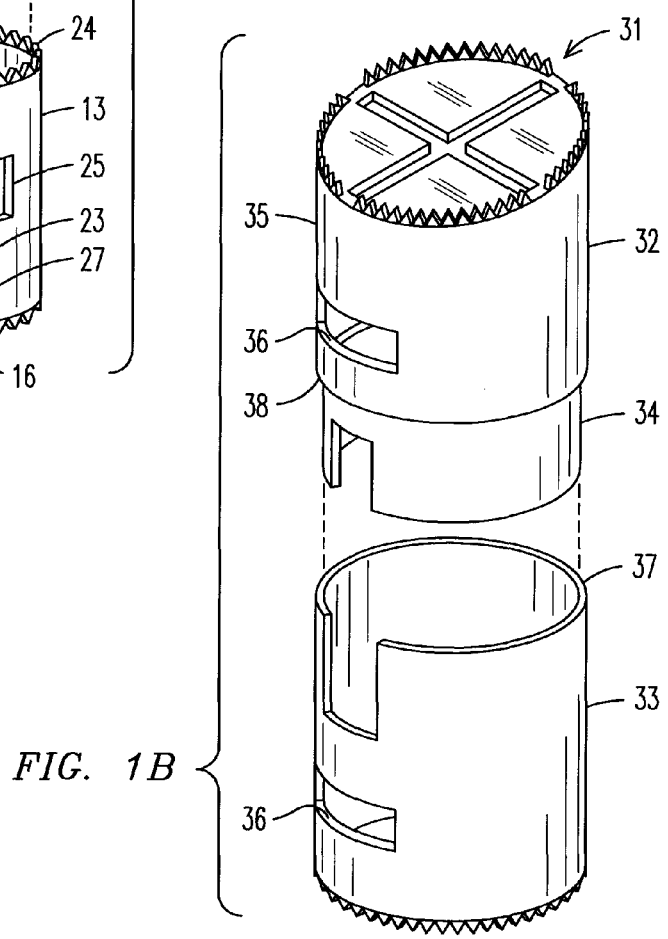

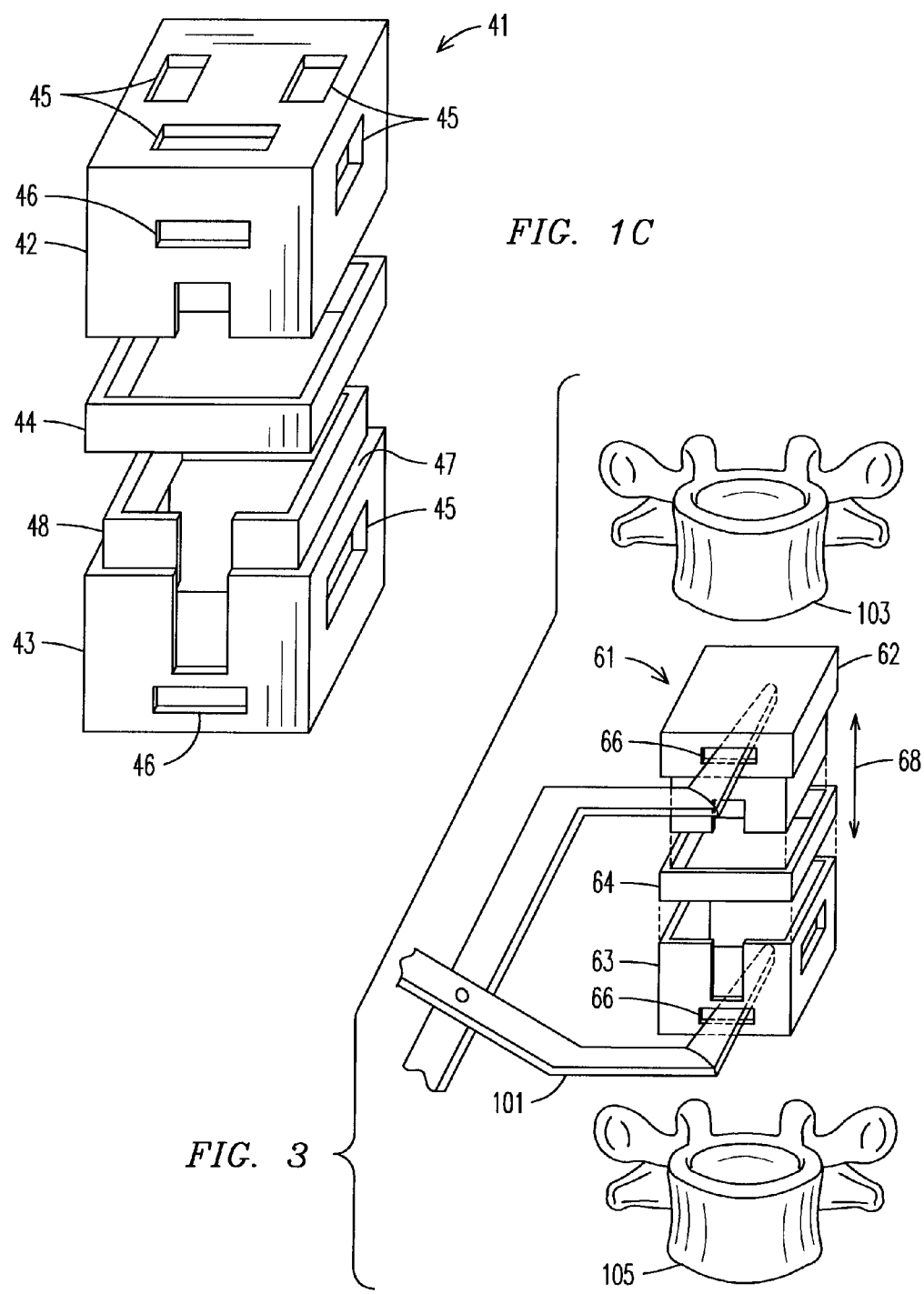

VERTEBRAL BODY REPLACEMENT

CROSS-REFERENCE TO RELATED APPLICATION

This application claims the benefit of U.S. provisional patent application No. 60/864,857, filed Nov. 8, 2006.

FIELD OF THE INVENTION

The present invention generally relates to a vertebral body replacement to be inserted into an intervertebral space, thereby supporting the spinal column of a patient. The present invention further relates to a system and method for expanding and distracting a vertebral body replacement element into and within the spinal column of a patient.

BACKGROUND OF THE INVENTION

Back pain is one of the most significant problems facing the workforce in the United States today, is a leading cause of sickness-related absenteeism, and the main cause of disability for people between the ages of 19 and 45. Back pain can occur from pinching or irritating a spinal nerve, compression of the spine, vertebral shifting relative to the spinal cord axis, and formation of bone spurs. The most common cause of disabling back pain, however, generally stems from trauma to a vertebral disc, such as from mechanical shock, stress, tumors, or degenerative diseases. In many cases, the disc can become permanently damaged or degenerated, such that the preferred treatment necessitates partial or total excision and replacement of the damaged disc.

Traumatic injury to a vertebral disc that is not removed frequently can promote scar tissue formation. Such scar tissue typically is thicker than the healthy tissue, such that the disc continues to progressively degenerate, lose water content, and can stiffen and become significantly less effective as a shock absorber. Eventually, the disc can deform, herniate, or collapse, eliminating the flexibility of the spinal column, and potentially leading to further degeneration or damage to other vertebral discs of the spinal column. At such a point, the only option is for the damaged disc to be partially or completely removed.

When the disc is partially or completely removed, generally it is necessary to replace the excised material to prevent direct contact between the boney surfaces of the adjacent vertebrate on either side of the removed disc. For example, U.S. Pat. No. 6,824,565 of Muhanna discloses a vertebral spacer that is inserted between adjacent vertebrate to provide restorative force and function as a shock absorber between the adjacent vertebrate. Another alternative approach has been to insert a "cage" that can maintain a space occupied by the removed disc to prevent the vertebrate from collapsing and impinging upon the nerve roots of the spine. Still further, spinal fusion has been used to restrict motion and stabilize patients' spines by fusing adjacent vertebrate together. This generally can reduce mechanical back pain by preventing the now immobile vertebrate from impinging on a spinal nerve; however, such stability and pain reduction generally is created at the expense of spinal flexibility and motion. In addition, many conventional techniques for disc repair and replacement can be limited in terms of their size or configuration and thus generally are not designed to accommodate variations in size of the gap resulting from the excising of the vertebral disc material. Further, conventional techniques often cannot accommodate expansion or growth of the spine, frequently requiring replacement of the vertebral spacers with other, different size spacers.

Accordingly, it can be seen that a need exists for a vertebral body replacement and system and method of implanting such a vertebral body replacement that addresses the forgoing related and unrelated problems in the art.

BRIEF DESCRIPTION OF THE DRAWINGS

FIGS. 1A-1C are perspective illustrations of various alternative embodiments of the vertebral body replacement member according to the principles of the present invention.

FIG. 3 is a perspective illustration, illustrating the distraction of the intervetebral body replacement member according to the principles of the present invention positioned between adjacent vertebrate of the patient's spine to enable insertion of a spacer therebetween.

DESCRIPTION OF THE INVENTION

Figure 2:
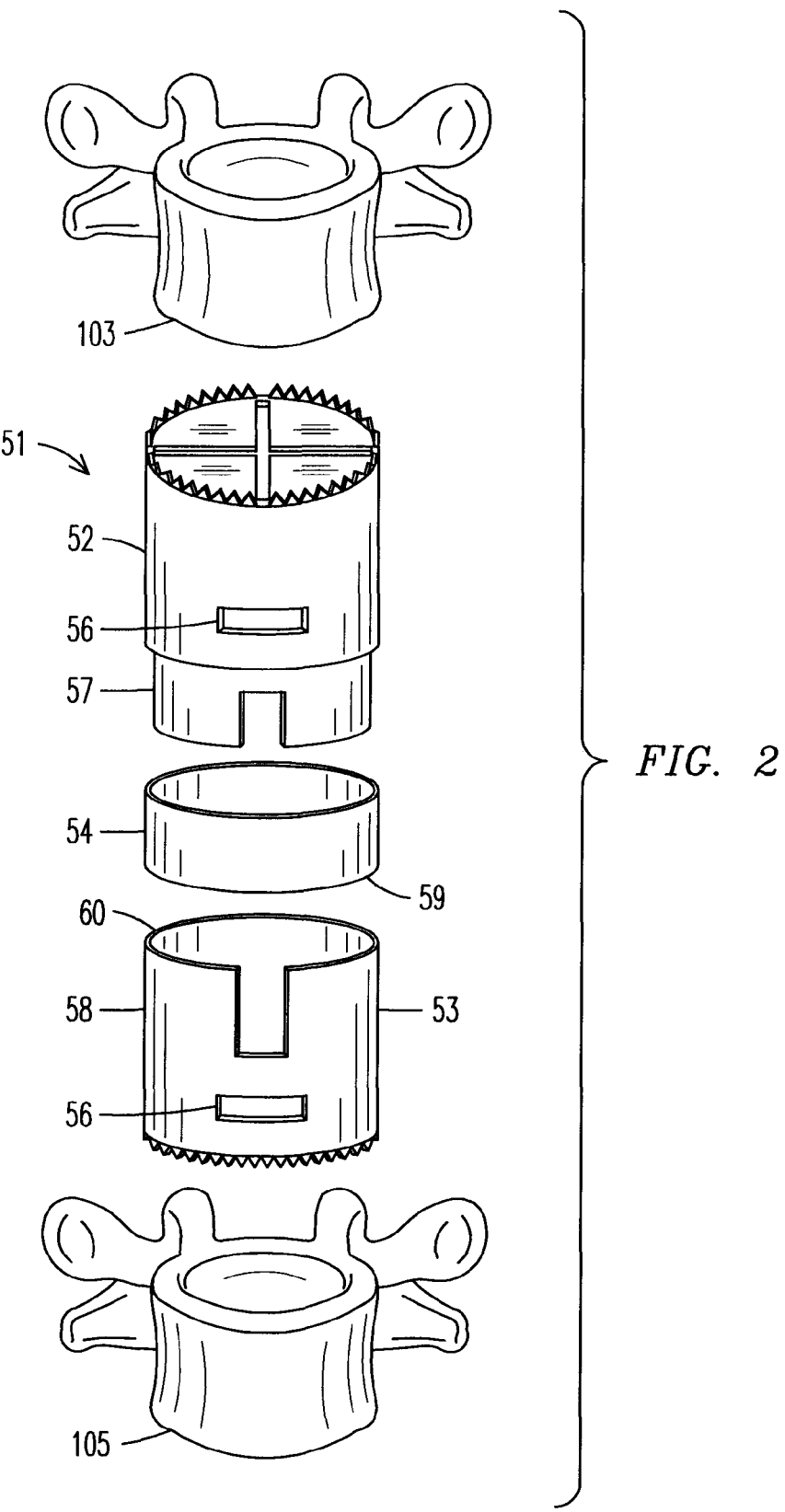
FIG. 2 is an exploded perspective illustrating the installation of the vertebral body replacement member such as illustrated in FIG. 1A or 1B within the spinal column of a patient.

As generally illustrated in FIGS. 1A-1C, the disclosed apparatus is directed to a vertebral body replacement member or elements for insertion into an intervertebral space or gap between vertebrae of a patient's spine to replace substantially all of a vertebral disc or vertebrae that has been excised or removed due to damage or degeneration of the disc. The vertebral body replacement member generally is useful to replace a vertebral disc that has degenerated due to traumatic injury, vertebral displacement, disease (i.e., autoimmune disease, rheumatoid arthritis, etc.), or any other pathological condition of the spinal column that may injure or shift the intervetebral discs. The vertebral body replacement member provides support to the adjacent vertebrae of the patient's spine to help maintain the separation between the vertebrae, while also preserving the natural curvature of the spine and further enabling regenerative bone growth and adjustment of the intervertebral spacing between the adjacent vertebrae to accommodate growth or expansion therebetween.

It is generally contemplated that the vertebral body replacement member can be made from any bio-compatible or physically inert material or combination of such materials having the mechanical strength capable of maintaining the intervetebral space between adjacent vertebrae, as indicated in FIGS. 2 and 3, without impinging upon nerves and/or restricting movement and further bone growth or regeneration of the spinal column discs adjacent the intervetebral space in which the disclosed apparatus is mounted. Examples of such materials can include bone, such as bone sections from a femur or other bones of the patient or from donors, metal materials such as titanium, titanium alloys, stainless steel, chrome, cobalt, and other, similar materials, as well as various polymeric materials such as methyl methacrylate (MMA), urethane, polyacetal material, reinforced polymers such as carbon fiber or polyether keytone, polycarbonates, polypropylene, polyamides, and silicone based polymers as generally understood in the art.

As illustrated in FIGS. 1A-1C, the vertebral body replacement member generally includes a telescoping construction, including an upper section and a lower section. Turning now to FIG. 1A, an upper section 12 and a lower section 13 of the vertebral body replacement member 11 engage or interface via a sliding joint which allows relative linear motion in the direction of an axis of linear motion 14. Assembly, adjustment, and removal of the vertebral body replacement member 11 is enhanced with the sliding joint because the sections advantageously move more freely than with other attachment or interfacing means. While alternate attachment or interfacing means may be available, an acceptable alternate does not include a threaded means. The upper section 12 and the lower section 13 can be formed in various configurations or cross sections. Such configurations generally include a cylindrical configuration, having a substantially circular cross section as illustrated in FIGS. 1B and 2; a generally cylindrical configuration with a substantially oval cross-section as illustrated in FIG. 1A; or in square or rectangular configurations as generally illustrated in FIGS. 1C and 3. Among other functions, the non-circular embodiments have the added benefit of restricting longitudinal rotation relative to the axis of linear motion 14 between the upper section 12 and the lower section 13. An alternate means of restricting longitudinal rotation between the upper and lower sections from those disclosed in FIGS. 1B and 1C would be a key and keyway interface (not illustrated). In some applications, restriction of longitudinal rotation is desired and is accomplished by the non-circular alternate embodiments. The circular configuration is advantageous in that although longitudinal rotation is not required, it is possible, while providing relative linear motion of the upper section 12 and the lower section 13. Further, as illustrated in FIG. 1A, with a top surface 15 and a bottom surface 16 angled or contoured as discussed below, restricting longitudinal rotation of the upper section 12 and the lower section 13 is desired. Each of the upper section 12 and the lower section 13 further generally includes an open-ended body formed from a bio-compatible or physically inert material as discussed above, and one of the sections, for example the upper section 12, will be formed with at least a portion of its body having a slightly smaller diameter or cross-sectional area than the lower section so as to telescope into and out of the open upper end of the lower section 13 as indicated in FIGS. 1A-1C. It will, however, also be understood that the upper section 12 and the lower section 13 can be formed with the lower section 13 telescoping into and out of the upper section 12 as needed or desired.

The open ended structures of the upper section 12 and the lower section 13 further generally define a space or cavity 17 within the vertebral body replacement member 11 as the two sections 12, 13 are brought together. The upper section 12 generally includes a substantially flat top surface 15 that further can include channels 18 or openings formed therein, and, as illustrated in FIGS. 1A and 1B, further can include a series of teeth or serrations 19 formed about the side edge 20 of the top surface 15 of the upper section 12 to help secure it against an adjacent upper vertebrae (not illustrated). The lower section 13 typically has a similar construction, with an open upper end, a closed, substantially flat bottom surface, and further generally includes slots or openings formed in its bottom or base plate. The lower section 13 also can include series of teeth or serrations 22 formed about the side edge 16 of its lower or bottom base plate to help engage and fix the lower section 13 to the lower vertebrae (not illustrated) of the patient's spine in which it is mounted. Additionally, an upper portion of the lower section 13 may also include teeth or serrations 24, further aiding in support of the component 11 to the vertebrae. The top surface 15 and the bottom surface of the upper section 12 and the lower section 13, respectively, additionally can be angled or contoured as needed to substantially match the contour of the adjacent upper and lower vertebrae on which the sections 12, 13 are mounted or engaged.

Openings 21, 25, 26 are formed in top 126 and bottom 27 portions of the upper section 12 and the lower section 13 of the vertebral body replacement member 11 and provide areas or points of access for bone to grow and expand into the surrounding tissue about the patient's spine to help further secure the vertebral body replacement member 11 within the patient's spine and to foster or facilitate regeneration and additional bone growth.

Opening 26 also provides a point of access for a tool (see FIG. 3, item 101) to install, adjust, or remove the vertebral body replacement member 11. As illustrated in FIG. 1C, growth openings 45 are also formed in the top and side walls thereof. The telescoping construction of the vertebral body replacement member 11 further enables the vertebral replacement member 11 to expand or extend as needed to accommodate such additional or regenerative bone growth and to enable further adjustment of the spacing provided by the vertebral body replacement member 11 as needed to fit the intervetebral space created by the excising or removal of part or the entirety of the damaged vertebral disc.

As further illustrated in FIGS. 1-3, the upper sections 12, 32, 42, 52, 62 and the lower sections 13, 33, 43, 53, 63 each generally include large slotted opening 26 openings 26, 36, 46, 56, 66 formed through the side wall or walls of the upper sections 12, 32, 42, 52, 62 and the lower sections 13, 33, 43, 53, 63 of the vertebral body replacement members 11, 31, 41, 51, 61. Referring to FIG. 1A, openings 21, 25, 26 enable the insertion and packing of bone material within the cavity 17 defined between the upper section 12 and the lower section 13 of the vertebral body replacement 11 member after implantation or placement of the vertebral body replacement member 11 within the patient's spine. Such implanted bone material can then fuse to and grow with the existing remaining vertebrae of the patient, expanding out through the openings 25, 26 formed in the top, bottom, and side walls of the upper section and side walls of the lower section, as well as opening 21 in the lower section of the vertebral body replacement member 11 and into contact with the adjacent upper and lower vertebrae and the tissue surrounding the patient's spine.

Alternate embodiments of the vertebral body replacement member are illustrated in FIGS. 1B and 1C. FIG. 1B illustrates a vertebral body replacement member 31 having an upper section 32 and a lower section 33. The upper section 32 and the lower section 33 assemble such that the two sections 32, 33 fit together in a telescopic fashion. The upper section 32 and the lower section 33 as illustrated are circular in cross section but can be oval in cross section, thus preventing relative rotation between the two sections 32, 33. In this embodiment, the upper section 32 has a lower portion or protrusion 34 with a reduced diameter from an upper portion 35. A lip 36 is formed at the interface of the upper portion 35 and the lower portion 34. When the upper section 32 and the lower section 33 are assembled, the lip 36 rests on, or comes into contact with, a rim 37 of the lower section 33 and establishes a length of the vertebral body replacement member 31. Illustrated in FIG. 1C, a vertebral body replacement member 41 is shown having an upper section 42 and a lower section 43 with the upper section 42 and lower section 43 being square, or rectangular, in cross section. The lower section 43 further comprises a protrusion 48. A spacer 45 fits between the upper section 42 and the lower section 43 and is restrained by contact with the protrusion 48, and establishes, among other things, a length of the vertebral replacement body member 41. The spacer 45 may also increase the overall rigidity of the component 11, help absorb shock during use, reduce component 41 wear, and reduce the amount of packing material necessary. When assembled, the spacer 45 may rest on a base 47 of the lower section 43.

Still further, as best illustrated in FIG. 3, the upper sections 12, 32, 42, 52, 62 and the lower sections 13, 33, 43, 53, 63 of the vertebral body replacement members 11, 31, 41, 51, 61 further generally will include a distraction slot 26, 36, 46, 56, 66 or similar opening for receiving a distracter instrument 65 or tool therein. Alignment of the distraction instrument 65 or tool with the distraction slot 26, 36, 46, 56, 66 is preserved because of the restriction of relative longitudinal rotation between the upper section and lower section in the non-circular embodiments (and the circular embodiment with keyways or other restrictive rotational restraints). The ends of the distracter instrument 65 will be introduced into the distraction slots 26, 36, 46, 56, 66 formed in the upper sections 12, 32, 42, 52, 62 and the lower sections 13, 33, 43, 53, 63 for placement of the vertebral body replacement members 11, 31, 41, 51, 61 within the vertebral space or excised area between the adjacent vertebrae 103, 105 and thereafter expanding the sections as needed by causing the upper sections 12, 32, 42, 52, 62 and the lower sections 13, 33, 43, 53, 63 to telescope or move outwardly in a direction of travel 68 away from each other so as to expand the intervertebral body replacement members 11, 31, 41, 51, 61 as needed to fill the intervertebral space.

In addition, as illustrated in FIGS. 2 and 3, one or more spacers 54, 64 also can be mounted between the upper and lower sections of the vertebral body replacement member as needed. The spacers 54, 64 generally will be made from the same or a compatible material as the upper section 52, 62 and the lower section 53, 63 of the vertebral body replacement member 51, 61 and typically will be of a similar configuration and/or size as the upper section and the lower section so as to fit therebetween without substantially overlapping the side edges of the upper section 52, 62 and the lower section 53, 63 and, provide a more mechanically robust and rugged structure due to the superior load carrying abilities of a nested structure in compression having a large load bearing surface. For example, as illustrated in FIG. 2, the upper section 52 of the vertebral body replacement member 51 can include a bottom portion 57 formed with a reduced area or diameter that is adapted to be received and telescope into the open upper end 58 of the lower section 53. The spacers 54 can be of a similar size and configuration as the upper section 52 and the lower section 53 so as to fit over this recessed portion 57 of the upper section 52 as indicated. The spacers 54 also can be provided with teeth (not shown) as needed to help secure the spacers in place within the intervertebral space, between the adjacent vertebrae 103, 105. The spacer 54 may be configured as a hollow ring, having an inner diameter that is similar to the diameter of the recessed portion 57. The ring shaped spacer 54 may also be a split ring to facilitate assembly. As a ring, the spacer 54 is free to slide telescopically along the recessed portion 57 so when assembled, the lower surface of the ring 59 will rest against the upper rim 60 of the lower section 53 thereby establishing the minimum length of the vertebral body replacement member 51.

The spacers 54 typically will be inserted as needed after implantation of the vertebral body replacement member 51 within the intervetebral space, by engagement of the upper section 52 and the lower section 53 of the vertebral body replacement 51 member by the distraction tool (see FIG. 3) and expansion thereof, so as to create a gap in which the spacer 54 or spacers 54 can be inserted. Thereafter, as the distraction instrument is closed, the upper section 52 and the lower section 53 of the vertebral body replacement member 51 will be brought together, sealing into engagement with each other and with any spacers 54 contained therebetween. Thereafter, the distraction tool or instrument can be removed and the surgical opening in the patient's back closed. Still further, if additional spacers 54 are needed, the distraction tool can be engaged with the slots in an upper slot 71 and a lower slot 72 and the upper section 52 and the lower section 53 further separated to enable implantation of a additional spacers 54 as needed.

The present invention thus provides a simple device, typically made from a single, biocompatible material with minimal parts and generally utilizing only a minimal presences of screws, if at all, or similar fasteners to attach the upper and lower sections of the vertebral body replacement member to the adjacent vertebrate of the patient. The vertebral body replacement member further is radiolucent and expandable, and any distraction required is done by distracting the device internally through the engagement of the distraction instrument with the slotted openings in the upper and lower sections thereof, such that there is no distraction or engagement of screws that could damage bone. The growth openings formed in the top, bottom and side walls of the upper and lower sections, respectively, further enable bone growth out of the vertebral body replacement member and into the surrounding bone and tissue to help promote healing and more natural freedom of movement, while maintaining the intervetebral space and preventing collapse of the patient's spine.

It will be understood by those skilled in the art that while the foregoing has been described with reference to preferred embodiments and features, various modifications, variations, changes and additions can be made thereto without departing from the spirit and scope of the invention.

What is claimed is:

1. An adjustable vertebral body replacement assembly configured to be arranged in an intervertebral space between adjacent vertebrae, comprising:
   a first component defining a body having a first end and an open second end; and
   a second component defining a body having a first section and a second section, the first section having a third end and a fourth end, and the second section having a cross-sectional area smaller than a cross-sectional area of the first section, the second section extending from the first section away from the fourth end and configured to telescope within a continuous range of positions within the open second end; and
   a removable spacer having a first spacer length and configured to be positioned around the second section and longitudinally entirely between said second end and said fourth end when the second section is within the open second end.

2. The adjustable vertebral body replacement assembly as claimed in claim 1, further comprising a plurality of removable spacers, each spacer having a spacer length and configured to be positioned around the second section when the second section is within the open second end.

3. The adjustable vertebral body replacement assembly as claimed in claim 1, wherein the spacer further comprises a central opening having an inner surface that contacts an outer surface of said second section.

4. The adjustable vertebral body replacement assembly as claimed in claim 3, further comprising an outer surface of the body of the second component and a lip formed on the fourth end of the second component between the second section and the outer surface.

5. The adjustable vertebral body replacement assembly as claimed in claim 4, wherein a vertebral body length of the vertebral body replacement assembly is adjusted by replacing said removable spacer having a first spacer length with a removable spacer having a second spacer length and a change in said vertebral body length is directly proportional to a difference between said first spacer length and said second spacer length.

6. The adjustable vertebral body replacement assembly as claimed in claim 1, wherein the first end and third end are substantially flat and are configured to contact adjacent vertebrae.

7. The adjustable vertebral body replacement assembly as claimed in claim 1, wherein the first component and the second component further comprise a plurality of openings or channels.

8. The adjustable vertebral body replacement assembly as claimed in claim 1, wherein the first end and the third end include a series of teeth or serrations to secure the first and second components to adjacent vertebrae.

9. The adjustable vertebral body replacement assembly as claimed in claim 1, further comprising a key and a keyway to resist relative rotation between the first component and the second component.

10. The adjustable vertebral body replacement assembly as claimed in claim 1, wherein the first component and the second component each have a distraction slot for receiving a first end and a second end of a distracter instrument.

11. The adjustable vertebral body replacement assembly as claimed in claim 1, wherein a cross section of the first component and a cross section of the second component are substantially circular.

12. The adjustable vertebral body replacement member as claimed in claim 1, wherein a cross section of the first component and a cross section of the second component are substantially rectangular or square.

13. The adjustable vertebral body replacement member as claimed in claim 1, wherein the second section is sized to create a sliding joint with no relative rotation between the first component and the second component.

14. The adjustable vertebral body replacement assembly as claimed in claim 1, wherein said first component, said second component and said second section collectively establish a sliding joint for axial motion, said sliding joint comprising smooth surfaces.

15. The adjustable vertebral body replacement assembly as claimed in claim 1, wherein a cross section of the first component and a cross section of the second component are substantially oval.

16. A kit for replacing a damaged vertebral disc in a spinal column, comprising:
   a vertebral body replacement assembly, comprising:
      a first component defining a first body having a first top and an open first bottom,
      a second component defining a second body having a second bottom, a second top, a first section, and a second section extending from the first section away from the second top, the second section having a cross-sectional area smaller than a cross-sectional area of the first section and the second section configured to telescope within the open first bottom toward and away from the first top; and
   at least one spacer configured to be removably mounted on said second section between the open first bottom and the second top, the at least one spacer configured to be positioned around the second section and longitudinally entirely between said open first bottom and said second top when the second section is within the open first bottom; and
   a distracter tool having a first arm for selectively engaging the first body and a second arm for selectively engaging the second body for installing, adjusting, and removing the vertebral body replacement assembly.

17. The kit as claimed in claim 16, wherein the first top and the second bottom include a series of teeth or serrations that are configured to contact adjacent vertebrae between which the vertebral body replacement assembly is installed.

18. The kit as claimed in claim 16, wherein a key and a keyway prevent relative rotation between the first component and the second component.

19. The kit as claimed in claim 16, further comprising a plurality of spacers, each spacer configured to be positioned around the second section when the second section is within the open first bottom.

20. The kit as claimed in claim 16, wherein a cross section of the first component and a cross section of the second component are substantially rectangular or square.

21. The kit as claimed in claim 16, wherein at least one of the first top and the second bottom are angled to match a contour of adjacent vertebrae.

22. The kit as claimed in claim 16, wherein said first arm is insertable into a recess on said first body and said second arm is insertable into a recess on said second body.

* * * * *

UNITED STATES PATENT AND TRADEMARK OFFICE
CERTIFICATE OF CORRECTION

| | | |
|---|---|---|
| PATENT NO. | : 8,920,502 B1 | Page 1 of 1 |
| APPLICATION NO. | : 11/937242 | |
| DATED | : December 30, 2014 | |
| INVENTOR(S) | : Nabil L. Muhanna | |

It is certified that error appears in the above-identified patent and that said Letters Patent is hereby corrected as shown below:

On the Title Page
Page 1 (item 57, Abstract) at line 9, Change "placement" to --replacement--.

In the Specification
In column 1 at line 47, Change "boney" to --bony--.
In column 2 at line 17 (approx.), Change "intervetebral" to --intervertebral--.
In column 2 at line 35, Change "intervetebral" to --intervertebral--.
In column 2 at line 46, Change "intervetebral" to --intervertebral--.
In column 2 at line 49, Change "intervetebral" to --intervertebral--.
In column 2 at line 57, Change "keytone," to --ketone,--.
In column 4 at line 16, Change "intervetebral" to --intervertebral--.
In column 4 at line 20, Change "opening 26 openings" to --openings--.
In column 4 at line 27, Change "replacement 11 member" to --replacement member 11--.
In column 5 at line 56, Change "intervetebral" to --intervertebral--.
In column 5 at line 58, Change "replacement 51 member" to --replacement member 51--.
In column 6 at line 22 (approx.), Change "intervetebral" to --intervertebral--.

In the Claims
In column 7 at line 29 (approx.), In Claim 12, change "member" to --assembly--.
In column 7 at line 33 (approx.), In Claim 13, change "member" to --assembly--.

Signed and Sealed this
Eighteenth Day of August, 2015

Michelle K. Lee
*Director of the United States Patent and Trademark Office*